United States Patent
Robinson et al.

(10) Patent No.: US 9,795,515 B2
(45) Date of Patent: Oct. 24, 2017

(54) MICRO-POROUS CONDUIT

(71) Applicant: KCI Licensing, Inc., San Antonio, TX (US)

(72) Inventors: Timothy Mark Robinson, Basingstoke (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 586 days.

(21) Appl. No.: 14/173,947

(22) Filed: Feb. 6, 2014

(65) Prior Publication Data

US 2014/0276489 A1    Sep. 18, 2014

Related U.S. Application Data

(60) Provisional application No. 61/782,713, filed on Mar. 14, 2013.

(51) Int. Cl.
*A61M 1/00* (2006.01)
*A61F 13/00* (2006.01)

(52) U.S. Cl.
CPC ..... *A61F 13/00068* (2013.01); *A61M 1/0025* (2014.02); *A61M 1/0084* (2013.01);
(Continued)

(58) Field of Classification Search
CPC ................................. A61F 13/00068
See application file for complete search history.

(56) References Cited

U.S. PATENT DOCUMENTS 1,355,846 A    10/1920    Rannells
2,547,758 A    4/1951    Keeling
(Continued)

FOREIGN PATENT DOCUMENTS

AU    550575 A1    3/1986
AU    745271    4/1999
(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

(Continued)

*Primary Examiner* — Tatyana Zalukaeva
*Assistant Examiner* — Sara Sass (57) ABSTRACT

A porous conduit may be suitable for use in treating a tissue site, and may include a central lumen and a porous wall positioned substantially concentric about the central lumen. The porous wall may have an open porous structure that may define a plurality of interconnected pores in fluid communication with one another. As part of a system, the porous conduit may be used with a manifold adapted to be positioned at a tissue site, a sealing drape adapted to cover the manifold to provide a sealed space relative to the tissue site, and a therapy device including a reduced-pressure source. The porous conduit may be disposed in the sealed space and in fluid communication between the sealed space and the reduced-pressure source.

20 Claims, 4 Drawing Sheets

(52) U.S. Cl.
CPC ....... *A61M 1/0088* (2013.01); *A61M 2205/15* (2013.01); *A61M 2205/3344* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,360,414 A | 11/1994 | Yarger | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,520,872 B2 * | 4/2009 | Biggie | A61M 1/0088 601/6 |
| 8,702,665 B2 * | 4/2014 | Locke | A61F 13/02 604/319 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2006/0079852 A1 | 4/2006 | Bubb et al. | |
| 2007/0218101 A1 * | 9/2007 | Johnson | A61B 17/88 424/423 |
| 2010/0042058 A1 * | 2/2010 | Casey | A61F 13/00068 604/290 |
| 2010/0106115 A1 * | 4/2010 | Hardman | A61M 1/0088 604/319 |
| 2011/0178481 A1 | 7/2011 | Locke et al. | |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| GB | 2466088 A | 6/2010 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |
| WO | 2010051071 A1 | 5/2010 |

(56) References Cited

FOREIGN PATENT DOCUMENTS

OTHER PUBLICATIONS

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ð ukić, Ž. Maksimović, Ð Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).
International Search Report and Written Opinion for corresponding PCT/US2014/015169 dated Jun. 4, 2014.
Twin Star Medical; http://twinstarmedical.com/technologies.html; "Microporous Catheters in Development".
Twin Star Medical; http://www.twinstarmedical.com/clinical_apps.html; "Cerebral Edema Management in Traumatic Brain Injury: The Twin Star Approach".
Chinese First Office Action corresponding to CN201480013496.4, dated Aug. 30, 2016.

\* cited by examiner

MICRO-POROUS CONDUIT

RELATED APPLICATION

This application claims the benefit, under 35 USC §119 (e), of the filing of U.S. Provisional Patent Application Ser. No. 61/782,713, entitled "MICRO-POROUS CONDUIT," filed Mar. 14, 2013, which is incorporated herein by reference for all purposes.

FIELD

This disclosure relates generally to medical treatment systems and, more particularly, but not by way of limitation, to micro-porous conduits, dressings, and systems suitable for use in treating a tissue site.

BACKGROUND

Depending on the medical circumstances, reduced pressure may be used for, among other things, reduced-pressure therapy to encourage granulation at a tissue site, draining fluids at a tissue site, closing a wound, reducing edema, promoting perfusion, and fluid management. Common conduits, dressings, and systems may be susceptible blockages that can cause a reduction in the effectiveness of the therapy or a complete loss of therapy. Such a situation can occur, for example, if the amount of fluid in the system exceeds the fluid capacity of the system. Blockages in conduits, for example, may prevent reduced pressure from reaching the tissue site and/or prevent accurate measurement of the reduced pressure at the tissue site for reduced pressure control. Thus, improvements to conduits, dressings, and systems that may enhance reliability are desirable.

SUMMARY

Shortcomings with certain aspects of tissue treatment dressings, systems, and methods are addressed as shown and described in a variety of illustrative, non-limiting embodiments herein.

In some embodiments, provided is a system for treating a tissue site that may include a manifold, a sealing drape, a porous conduit, and a therapy device. The manifold may be adapted to be positioned proximate the tissue site. The sealing drape may be adapted to cover the manifold and the tissue site to provide a sealed space between the sealing drape and the tissue site. The porous conduit may be adapted to be in fluid communication with the manifold and the sealed space. The porous conduit may include a central lumen, a first porous wall, a barrier layer, and a second porous wall. The first porous wall may be positioned substantially concentric about the central lumen. The first porous wall may have an open porous structure defining a plurality of interconnected pores in fluid communication with one another. The barrier layer may be positioned substantially concentric about the first porous wall. The barrier layer may be comprised of a non-porous material. The second porous wall may be positioned substantially concentric about the barrier layer. The second porous wall may have an open porous structure defining a plurality of interconnected pores in fluid communication with one another. The barrier layer may substantially preclude fluid communication laterally between the first porous wall and the second porous wall. The therapy device may be adapted to be in fluid communication with the porous conduit.

In other embodiments, provided is a system for treating a tissue site that may include a manifold, a sealing drape, a porous conduit, and a therapy device. The manifold may be adapted to be positioned proximate the tissue site. The sealing drape may be adapted to cover the manifold and the tissue site to provide a sealed space between the sealing drape and the tissue site. The porous conduit may be adapted to be disposed in the sealed space in fluid communication with the manifold and the sealed space. The porous conduit may include a central lumen and a porous wall. The porous wall may be positioned substantially concentric about the central lumen. The porous wall may have an open porous structure defining a plurality of interconnected pores in fluid communication with one another. The therapy device may be adapted to be in fluid communication with the porous conduit. The therapy device may include a reduced-pressure source and a pressure sensor. The reduced-pressure source may be adapted to be in fluid communication with the central lumen, and the pressure sensor may be adapted to be in fluid communication with the porous wall.

In other embodiments, provided is a system for treating a tissue site that may include a manifold, a sealing drape, a porous conduit, and a therapy device. The manifold may be adapted to be positioned proximate the tissue site and to distribute reduced pressure to the tissue site. The sealing drape may be adapted to cover the manifold and the tissue site to provide a sealed space between the sealing drape and the tissue site. The porous conduit may be adapted to be disposed in the sealed space in fluid communication with the manifold and the sealed space. The porous conduit may include a central lumen, a first porous wall, a barrier layer, and a second porous wall. The first porous wall may be positioned substantially concentric about the central lumen. The first porous wall may have an open porous structure defining a plurality of interconnected pores in fluid communication with one another. The first porous wall may be comprised of bonded particles defining the interconnected pores. The bonded particles may be sintered polymer particles. The barrier layer may be positioned substantially concentric about the first porous wall. The barrier layer may be comprised of a non-porous, liquid impermeable material. The second porous wall may be positioned substantially concentric about the barrier layer. The second porous wall may have an open porous structure defining a plurality of interconnected pores in fluid communication with one another. The second porous wall may be comprised of bonded particles defining the interconnected pores. The bonded particles may be sintered polymer particles. The barrier layer may substantially preclude fluid communication laterally between the first porous wall and the second porous wall. The therapy device may be adapted to be in fluid communication with the porous conduit. The therapy device may include a reduced-pressure source, a fluid instillation source, and a pressure sensor. The reduced-pressure source may be in fluid communication with the central lumen, the fluid instillation source may be in fluid communication with the first porous wall, and the pressure sensor may be in fluid communication with the second porous wall.

Other aspects, features, and advantages of the illustrative embodiments will become apparent with reference to the drawings and detailed description that follow.

BRIEF DESCRIPTION OF THE DRAWINGS

A more complete understanding of this specification may be obtained by reference to the following detailed description when taken in conjunction with the accompanying drawings wherein.

DETAILED DESCRIPTION OF ILLUSTRATIVE EMBODIMENTS

In the following detailed description of the non-limiting, illustrative embodiments, reference is made to the accompanying drawings that form a part hereof. Other embodiments may be utilized, and logical, structural, mechanical, electrical, and chemical changes may be made without departing from the scope of this specification. To avoid detail not necessary to enable those skilled in the art to practice the embodiments described herein, the description may omit certain information known to those skilled in the art. The following detailed description is provided without limitation and with the scope of the illustrative embodiments being defined by the appended claims.

Figure 1:
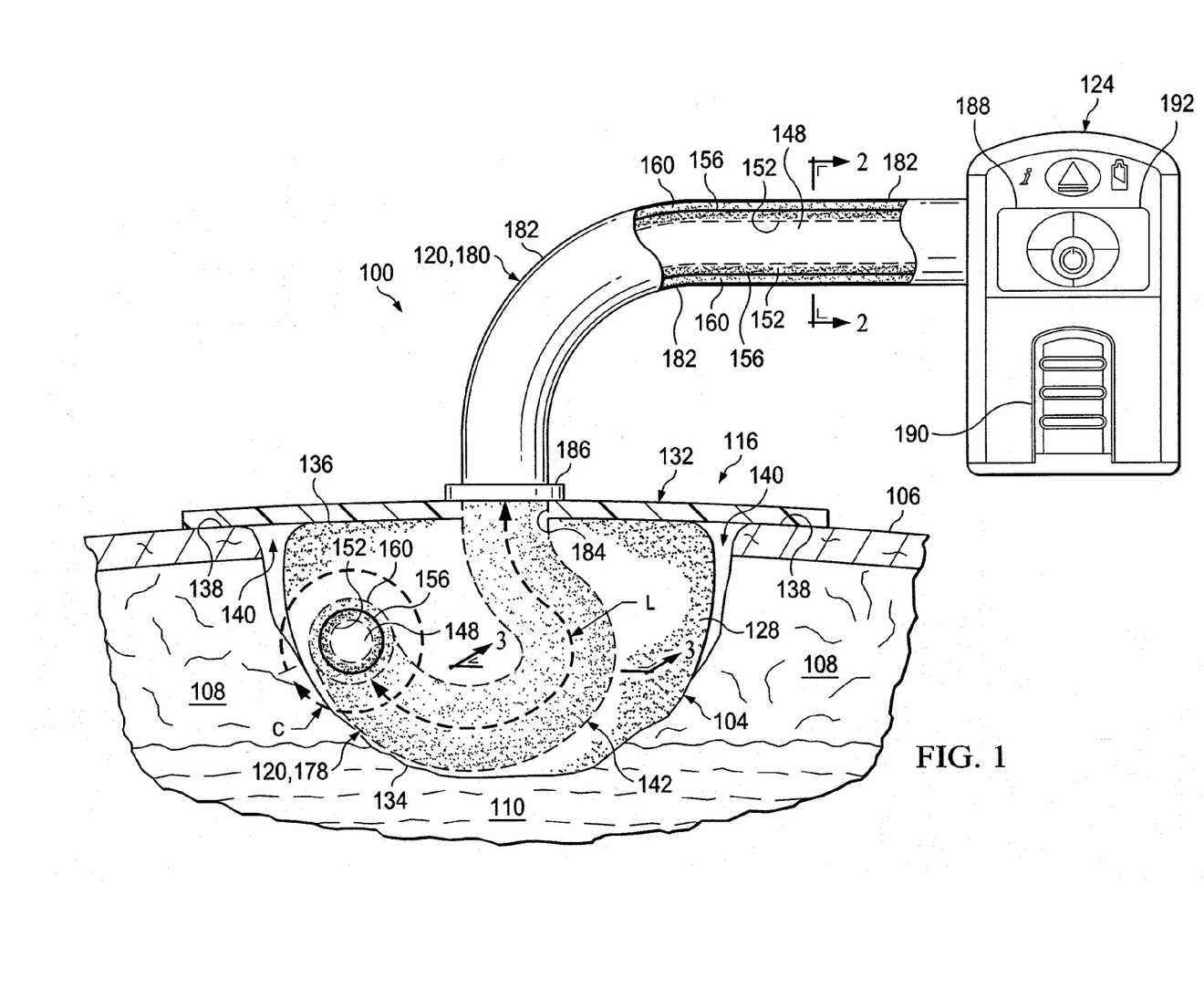
FIG. 1 illustrates an embodiment of a system for treating a tissue site, with a portion shown in cut-away view, depicting an illustrative embodiment of a porous conduit according to this disclosure.

Referring to the drawings, provided is a system 100 for treating a tissue site 104 that may be suitable for use with reduced pressure. The tissue site 104 may extend through or otherwise involve an epidermis 106, a dermis 108, and a subcutaneous tissue 110. The tissue site 104 may be a sub-surface tissue site as depicted in FIG. 1 that extends below the surface of the epidermis 106. Further, the tissue site 104 may be a surface tissue site (not shown) that predominantly resides on the surface of the epidermis 106. The system 100 may provide therapy to, for example, the epidermis 106, the dermis 108, and the subcutaneous tissue 110, regardless of the positioning of the system 100 or the type of tissue site. The system 100 may also be utilized without limitation at other tissue sites.

Further, the tissue site 104 may be the bodily tissue of any human, animal, or other organism, including bone tissue, adipose tissue, muscle tissue, dermal tissue, vascular tissue, connective tissue, cartilage, tendons, ligaments, or any other tissue. Treatment of the tissue site 104 may include removal of fluids, e.g., exudate or ascites. As described below, components of the system 100 may be fluidly coupled to each other to provide a path for transferring fluids (e.g., liquid and/or gas) between the components. As used herein, unless otherwise indicated, "or" does not require mutual exclusivity.

Figure 2:
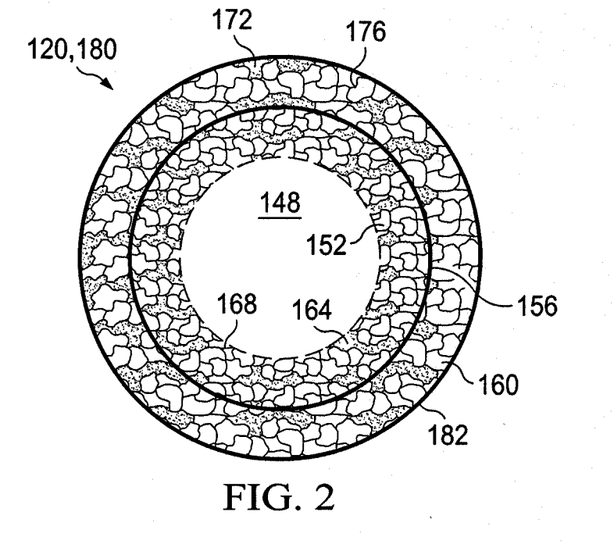
FIG. 2 illustrates a cross-section view of an external end of the porous conduit of FIG. 1 taken at line 2-2 in FIG. 1.
Figure 3:
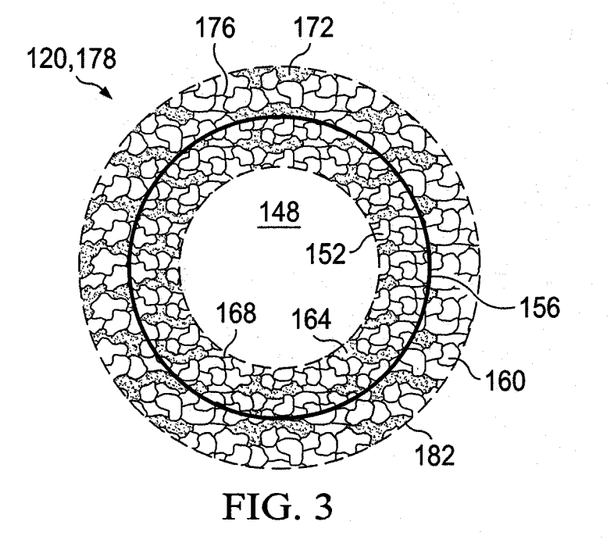
FIG. 3 illustrates a cross-section view of an insertion end of the porous conduit of FIG. 1 taken at line 3-3 in FIG. 1.

Referring to FIGS. 1-3, in some illustrative embodiments, the system 100 may include a dressing 116, a porous conduit 120, and a therapy device 124. The dressing 116 may include a manifold 128 and a sealing drape 132. The manifold 128 may have a first side 134 and a second side 136. The first side 134 of the manifold 128 may be adapted to be positioned within, over, proximate to, adjacent to, facing, or in contact with the tissue site 104. The manifold 128 may take many forms, and may be any size, shape, or thickness depending on a variety of factors, such as the type of therapy being implemented or the nature and size of a particular tissue site. The manifold 128 may, for example, be cut or otherwise shaped to fit the particular size and shape of the tissue site 104 in any suitable manner.

The manifold 128 may be a substance or structure capable of applying reduced pressure to, delivering fluids to, or removing fluids from the tissue site 104. In some embodiments, the manifold 128 may be used to distribute fluids such as medications, antibacterials, growth factors, and various solutions to the tissue site 104. For example, the manifold 128 may be a porous and permeable foam or foam-like material including a plurality of flow channels or pathways that distribute fluids to and remove fluids from the tissue site 104. The manifold 128 may include, without limitation, devices that have structural elements arranged to form flow channels, such as, cellular foam, open-cell foam, porous tissue collections, liquids, gels, and foams that include, or cure to include, flow channels. Additionally, the manifold 128 may be a gauze, felted mat, or any other material suited to a particular biological application.

In some embodiments, the manifold 128 may be a porous, hydrophobic material such as a polyurethane, open-cell reticulated foam manufactured under the trade name Granu-Foam® by Kinetic Concepts, Inc. of San Antonio, Tex. Other layers may be included in or on the manifold 128, such as absorptive materials, wicking materials, hydrophobic materials, and hydrophilic materials.

The sealing drape 132 may be adapted to cover the second side 136 of the manifold 128 and to seal to a peripheral surface 138 proximate the tissue site 104. The peripheral surface 138 may be undamaged epidermis 106 peripheral to the tissue site 104. In this manner, the sealing drape 132 may provide a fluid seal between the sealing drape 132 and the tissue site 104 with the second side 136 of the manifold 128 facing the sealing drape 132. In some embodiments, the manifold 128 may be positioned between the tissue site 104 and the sealing drape 132. The fluid seal provided by the sealing drape 132 may be a seal adequate to hold reduced pressure at a desired tissue site given the particular reduced-pressure source involved. Thus, the sealing drape 132 may provide a sealed space 140 proximate to the tissue site 104 that may be substantially isolated from the external environment and capable of maintaining reduced pressure.

The sealing drape 132 may comprise any material suitable for providing the fluid seal described above. For example, the sealing drape 132 may comprise one or more of the following materials: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Expopack Advanced Coatings of Wrexham, United Kingdom; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Pasadena, Calif.; polyether block polyamide copolymer (PEBAX), for example, from Arkema, France; or other appropriate material. Further, the sealing drape 132 may be a hybrid drape formed of a combination of the previously described materials.

In some embodiments, the sealing drape 132 may be comprised of a liquid impermeable material that may allow vapor and inhibit liquids from exiting the sealed space 140 of the dressing 116. The sealing drape 132 may be a flexible, breathable film having a high Moisture Vapor Transfer Rate (MVTR) of, for example, at least about 300 g/m² per 24 hours. The sealing drape 132 may comprise a range of medically approved films having a thickness between about 15 microns (μm) to about 50 microns (μm). In other embodiments, a low or no vapor transfer drape might be used.

In some embodiments, the dressing 116 may also include additional layers (not shown) that may be positioned between the tissue site 104 and the sealing drape 132. For example, the dressing 132 may include an absorption layer, a tissue-interface layer, or additional manifold layers. The dressing 116 may also include an attachment device (not shown) capable of adhering or otherwise sealing the sealing drape 132 to the peripheral surface 138. The attachment device may include, for example, silicones and hot-melt adhesives. Other suitable attachment devices may include, for example, hydrogels and hydrocolloids.

Continuing with the embodiments of FIGS. 1-3, the porous conduit 120 may include a central lumen 148, a first porous wall 152, a barrier layer 156, and a second porous wall 160. The porous conduit 120 may be adapted to be positioned in fluid communication with the manifold 128 and the sealed space 140. For example, the porous conduit 120 may be disposed in the sealed space 140 in fluid communication with the manifold 128 and the sealed space 140. As shown in the embodiment of FIG. 1, the porous conduit 120 may have an inserted length L into the sealed space 140 and an external circumference C that define an external surface area 142. The external surface area 142 may be in fluid communication with the manifold 128 and the sealed space 140. In some embodiments, the porous conduit 120 may be disposed into or around the manifold 128 with the external surface area 142 positioned in contact with the manifold 128.

The first porous wall 152 may be positioned substantially concentric about the central lumen 148 and in fluid communication with the central lumen 148. Further, the first porous wall 152 and the central lumen 148 may each be in fluid communication with the manifold 128 and the sealed space 140. For example, the first porous wall 152 may have an open porous structure defining a plurality of interconnected pores 164, shown in FIGS. 2 and 3, in fluid communication with one another. The open porous structure of the first porous wall 152 may be comprised of bonded particles 168, shown in FIGS. 2 and 3, defining the interconnected pores 164. The bonded particles 168 may be, for example, sintered polymer particles or fibers. Thus, the interconnected pores 164 of the first porous wall 152 may provide a plurality of fluid passageways through and along the length of the first porous wall 152 that may be in fluid communication with the central lumen 148, the manifold 128, and the sealed space 140.

The barrier layer 156 may be positioned substantially concentric about the first porous wall 152. The barrier layer 156 may be, for example, comprised of a material that is liquid impermeable and/or non-porous. The material comprising the barrier layer 156 may also be a hydrophobic material. The barrier layer 156 may be applied as part of the porous conduit 120, for example, through a co-extrusion process or during molding. In some embodiments, an internal barrier layer (not shown) may be disposed adjacent the first porous wall 152 within the central lumen 148. The internal barrier layer may be comprised of a similar material described above for the barrier layer 156.

The second porous wall 160 may be positioned substantially concentric about the barrier layer 156. Similar to the first porous wall 152, the second porous wall 160 may have an open porous structure defining a plurality of interconnected pores 172, shown in FIGS. 2 and 3, in fluid communication with one another. Further, the second porous wall 160 may be comprised of bonded particles 176, shown in FIGS. 2 and 3, defining the interconnected pores 172. Similar to the bonded particles 168 of the first porous wall 152, the bonded particles 176 of the second porous wall 160 may be, for example, sintered polymer particles or fibers. Also similar to the first porous wall 152, the interconnected pores 172 of the second porous wall 160 may provide a plurality of fluid passageways through and along the length of the second porous wall 160 that may be in fluid communication with the manifold 128 and the sealed space 140. The barrier layer 156 may substantially preclude fluid communication across or through the barrier layer 156 in a lateral direction between the first porous wall 152 and the second porous wall 160.

Continuing with FIGS. 1-3, the porous conduit 120 may have an insertion end 178, depicted in FIGS. 1 and 3, positioned within the sealed space 140, and an external end 180, depicted in FIGS. 1 and 2, positioned exterior to the sealed space 140. Although the insertion end 178 is shown in a curved configuration in FIG. 1, the insertion end 178 may extend straight or in any other suitable configuration within the sealed space 140. The second porous wall 160 of the insertion end 178 may define the inserted length L and the external circumference C of the porous conduit 120 as described above. The external end 180 of the porous conduit 120 may additionally include an external barrier layer 182 positioned substantially concentric about the second porous wall 160. Similar to the barrier layer 156 described above, the external barrier layer 182 may be comprised of a liquid impermeable and/or non-porous material that may also be a hydrophobic material. The external end 180 of the porous conduit 120 may protrude through an aperture 184 in the sealing drape 132 to be coupled in fluid communication to the therapy device 124. A sealing collar 186 may be sealingly engaged between the aperture 184 in the sealing drape 132 and the external end 180 of the porous conduit 120. The porous conduit 120 may be initially produced having the external barrier layer 182 applied as described above, with the external barrier layer 182 being subsequently removed along the length L of the insertion end 178. For example, the external barrier layer 182 may be removed through various post production processes such as milling, laser etching, particle erosion, or cutting prior to inserting the insertion end 178 into the sealed space 140.

In other embodiments (not shown), additional lumens (not shown) may be integrated into the porous conduit 120 as necessary to suit a particular application. For example, the central lumen 148 may be divided into two or more smaller lumens that may be positioned in a substantially flat configuration beside one another. Such a configuration may enhance patient comfort by providing a low profile for the porous conduit 120 and the system 100 that may be less likely to snag on clothing and other obstacles.

The therapy device 124 and the porous conduit 120 may be adapted to be in fluid communication with one another. As shown in FIG. 1, for example, the external end 180 of the porous conduit 120 may be coupled in fluid communication to the therapy device 124. The therapy device 124 may include a reduced-pressure source 188, a fluid instillation source 190, and a pressure sensor 192. The reduced-pressure source 188 may be coupled in fluid communication with the central lumen 148. The fluid instillation source 190 may be coupled in fluid communication with the first porous wall 152. The pressure sensor 192 may be coupled in fluid communication with the second porous wall 160. The reduced-pressure source 188, the fluid instillation source 190, and the pressure sensor 192 may be coupled in fluid communication to the components of the porous conduit 120 as described herein in any suitable manner. For example, the therapy device 124 may include a coupling (not shown) having fluid passageways adapted to provide fluid communication between the central lumen 148 and the reduced-pressure source 188, between the first porous wall 152 and the fluid instillation source 190, and between the second porous wall 160 and the pressure sensor 192.

The reduced-pressure source 188 may provide reduced pressure as a part of the system 100. The reduced-pressure source 188 may be any device for supplying a reduced pressure, such as a vacuum pump, wall suction, micropump, or other source. As shown in FIG. 1, the reduced-pressure source 188 may be housed within the therapy device 124. However, in some embodiments, the reduced-pressure source 188 may be a separate component in fluid communication with the central lumen 148 of the porous conduit 120. While the amount and nature of reduced pressure applied to a tissue site may vary according to the treatment application, the reduced pressure may be between about −5 mm Hg (−667 Pa) to about −500 mm Hg (−66.7 kPa). In some embodiments, the reduced pressure may be between about −75 mm Hg (−9.9 kPa) to about −300 mm Hg (−39.9 kPa).

The term reduced pressure may refer to a pressure less than the ambient pressure at the tissue site being subjected to treatment. The reduced pressure may be less than the atmospheric pressure, and less than a hydrostatic pressure at a tissue site. Unless otherwise indicated, values of pressure stated herein are gauge pressures. Consistent with the use herein, an increase in reduced pressure or vacuum pressure may refer to a relative reduction in absolute pressure.

As shown in FIG. 1, the fluid instillation source 190 may be housed within the therapy device 124. However, in some embodiments, the fluid instillation source 190 may be a separate component that may be in fluid communication with the first porous wall 152 of the porous conduit 120. The fluid instillation source 190 may be any device capable of containing and supplying a fluid for instillation in the system 100, such as, for example, a bladder or intravenous (IV) bag. The instillation fluid may be, for example, medications, anti-bacterials, growth factors, and other solutions as described above.

Further, as shown in FIG. 1, the pressure sensor 192 may be housed within the therapy device 124. However, in some embodiments, the pressure sensor 192 may be a separate component that may be in fluid communication with the second porous wall 160 of the porous conduit 120. The pressure sensor 192 may be any device suitable for sensing a reduced pressure and providing a pressure signal corresponding to the reduced pressure. In some embodiments, an indicator dye (not shown) may be included in the second porous wall 160 to indicate to a user that the second porous wall 160 has been exposed to fluid that could disrupt the pressure signal from the pressure sensor 192. For example, the indicator dye may be a material adapted to provide a color change when brought into contact with a liquid. The indicator dye may, for example, be disposed in at least a portion of the interconnected pores 172 of the second porous wall 160. The indicator dye may be utilized in other components of the system 100 without limitation.

Figure 4:
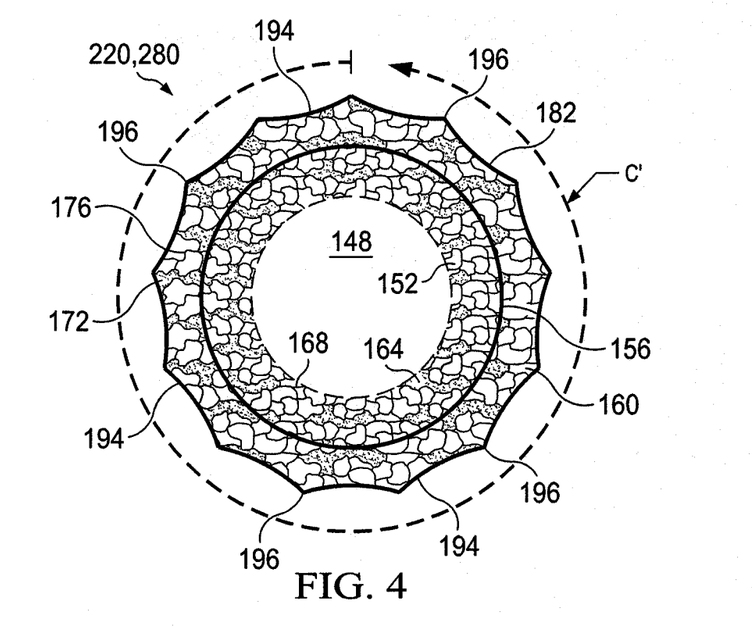
FIG. 4 illustrates a cross-section view of another embodiment of a porous conduit suitable for use with the system of FIG. 1.

In some embodiments, the porous conduit 120 may have a variety of shapes and geometries to suit a particular application. For example, geometries such as ovals, rectangles, and polygons may be utilized for the cross-sectional shape of the porous conduit 120. As shown in FIG. 4, an external end 280 of a porous conduit 220 may include a plurality of longitudinal depressions 194 and a plurality of longitudinal protrusions 196 suitable for use with the system 100. The longitudinal depressions 194 and the longitudinal protrusions 196 may be disposed about an external circumference C' of the porous conduit 220 and extend lengthwise along a length of the porous conduit 220. The porous conduit 220 may retain substantially the same structure and function of the previously described central lumen 148, the first porous wall 152, the barrier layer 156, the second porous wall 160, the external barrier layer 182, and other components of the porous conduit 120. Further, the porous conduit 220 may retain substantially the same integration as the previously described porous conduit 120 within the system 100. However, the longitudinal depressions 194 and the longitudinal protrusions 196 of the porous conduit 220 may provide additional external surface area for enhancing fluid communication, for example, with the sealed space 140 and the manifold 128 in the system 100.

Figure 5:
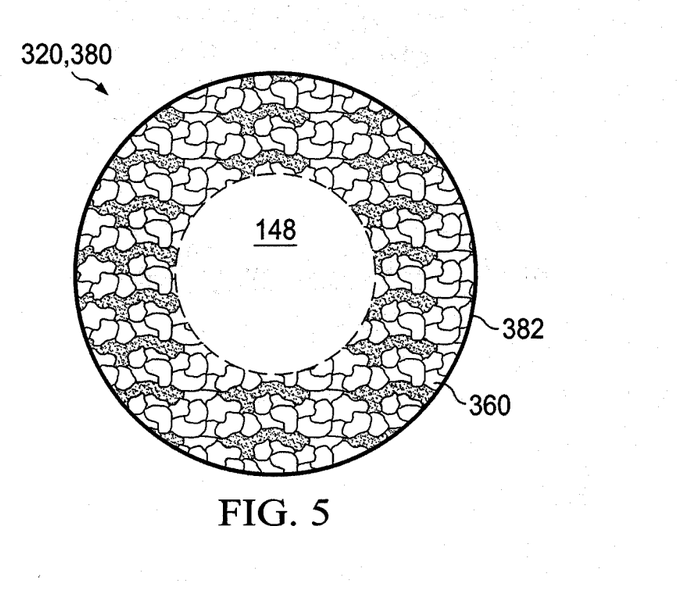
FIG. 5 illustrates a cross-section view of another embodiment of a porous conduit suitable for use with the system of FIG. 1.

In other embodiments, the porous conduit 120 may have any number of porous walls, analogous to the first and the second porous walls 152, 160, to suit a particular application. Likewise, barrier layers in the porous conduit 120 that may be analogous to the barrier layer 156 and the external barrier layer 182 may be added or omitted as necessary. For example, FIG. 5 illustrates another embodiment of a porous conduit 320 suitable for use in the system 100 in substantially the same manner as described above for the porous conduit 120. The porous conduit 320 may include the central lumen 148 and a porous wall 360 positioned substantially concentric about the central lumen 148 and in fluid communication with the central lumen 148. The central lumen 148 and the porous wall 360 may be positioned as described above in fluid communication with the sealed space 140 and the manifold 128. The porous wall 360 may have the same open porous structure and may be comprised of the same materials described above for the first porous wall 152 and the second porous wall 160. As described above, the central lumen 148 may be coupled in fluid communication with the reduced-pressure source 188. Analogous to the first and the second porous wall 152, 160, the porous wall 360 may be coupled in fluid communication with the pressure sensor 192 and/or the fluid instillation source 190 in the therapy device 124 as desired. Also analogous to the porous conduit 120, an external end 380 of the porous conduit 320 that may be adapted to be positioned exterior to the sealed space 140 may include an external barrier layer 382 comprised of substantially the same materials and having substantially the same structure as the external barrier layer 182.

Figure 6:
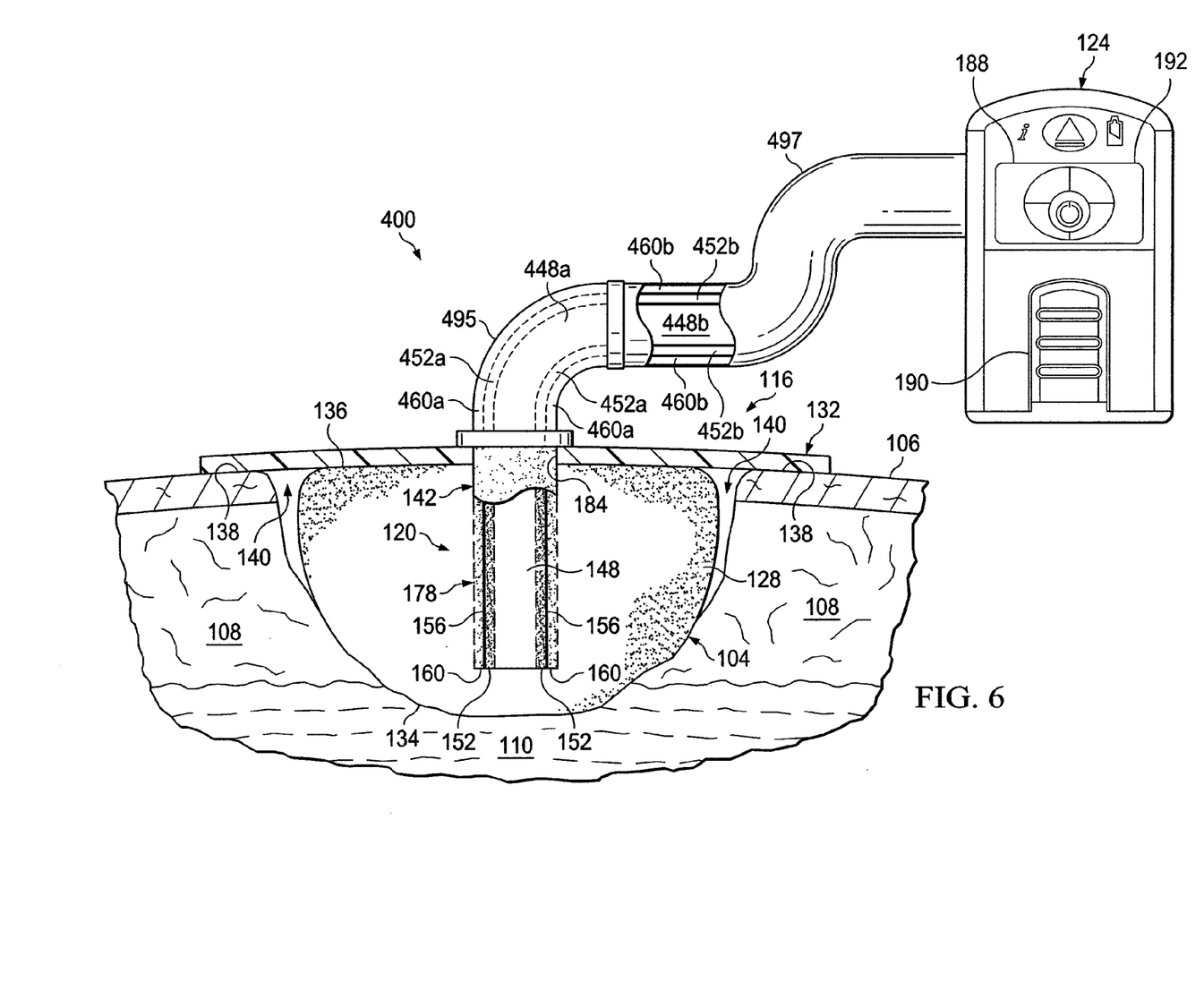
FIG. 6 illustrates another embodiment of a system for treating a tissue site, with a portion shown in cut-away view, depicting the porous conduit of FIG. 1 adapted for use with a conduit interface and a multiple lumen conduit.

Referring generally to FIG. 6, provided is an illustrative embodiment of a system 400 wherein the porous conduit 120 may be adapted for use with a conduit interface 495 and a multiple lumen conduit 497. The system 400 may be substantially similar in structure and function as the system 100. However, in the system 400, the insertion end 178 of the porous conduit 120 may be coupled in fluid communication with the conduit interface 495. Further, the insertion end 178 of the porous conduit 120 may be positioned in a substantially straight configuration within the sealed space 140.

Continuing with FIG. 6, the conduit interface 495 may be adapted to be coupled in fluid communication between the porous conduit 120 and the therapy device 124. As described above, the porous conduit 120 may be positioned in the sealed space 140 proximate the aperture 184 in the sealing drape 132. The conduit interface 495 may be coupled to the porous conduit 120 through the aperture 184 and may sealingly engage the sealing drape 132 about the aperture 184. Other embodiments (not shown) may include an external end of the porous conduit 120, analogous to the external end 180 depicted in FIG. 1, that may be adapted to be positioned exterior to the sealed space 140 and coupled in fluid communication to the conduit interface 495. In such an embodiment, the conduit interface 495 may remain separate from the sealing drape 132.

The conduit interface 495 may include a reduced-pressure lumen 448a that may be in fluid communication between the central lumen 148 and the reduced-pressure source 188. Further, the conduit interface 495 may include a fluid instillation lumen 452a that may be in fluid communication between the first porous wall 152 and the fluid instillation source 190. Additionally, the conduit interface 495 may include a sensing lumen 460a that may be in fluid communication between the second porous wall 160 and the pressure sensor 192. The conduit interface 495 may include any number of lumens as appropriate for providing fluid communication among embodiments of the porous conduit, the multiple lumen conduit, and the therapy device according to this disclosure.

The multiple lumen conduit 497 may be adapted to be coupled in fluid communication between the conduit interface 495 and the therapy device 124. Analogous to the conduit interface 495, the multiple lumen conduit 497 may include a reduced-pressure lumen 448b that may be in fluid communication between the central lumen 148 and the reduced-pressure source 188. Further, the multiple lumen conduit 497 may include a fluid instillation lumen 452b that may be in fluid communication between the first porous wall 152 and the fluid instillation source 190. Additionally, the multiple lumen conduit 497 may include a sensing lumen 460b that may be in fluid communication between the second porous wall 160 and the pressure sensor 192. The reduced-pressure lumen 448b, the fluid instillation lumen 452b, and the sensing lumen 460b of the multiple lumen conduit 497 may be in fluid communication with the reduced-pressure lumen 448a, the fluid instillation lumen 452a, and the sensing lumen 460a of the conduit interface 495, respectively. The multiple lumen conduit 497 may include any number of lumens as appropriate for providing fluid communication among embodiments of the porous conduit, the conduit interface, and the therapy device according to this disclosure.

In operation, the system 100 may be applied to a patient in the operating room after a surgical procedure or elsewhere. According to one illustrative embodiment, the manifold 128 may be placed proximate to the tissue site 104. The manifold 128 may be placed within the tissue site 104, or may overlay a portion of the tissue site 104. The sealing drape 132 may be placed over the manifold 128 such that a portion of the sealing drape 132 overlays the peripheral surface 138 around the tissue site 104. The sealing drape 132 may be secured to the peripheral surface 138 in order to form the sealed space 140 between the tissue site 104 and the sealing drape 132 described above. The fluid seal forming the sealed space 140 need only be adequate to allow the system 100 to maintain a reduced pressure at the tissue site 104 for a desired treatment time. The individual components of the dressing 116 may be sized according to the particular application or the procedure being performed by a healthcare provider. For example, the components of the dressing 116 may be sized, shaped, and configured to work in different anatomical applications such as the abdomen, chest, thighs, hip, etc.

The porous conduit 120 may be fed through the aperture 184 in the sealing drape 132 and pushed into the manifold 128, or fed between the manifold 128 and the tissue site 104. To assist with the application of the system 100, the manifold 128 may be pre-cut with holes (not shown) sized to receive the porous conduit 120. In some embodiments, the porous conduit 120 may be routed around the tissue site 104 and the manifold 128 may be subsequently applied allowing for a portion of the porous conduit 120 to be positioned proximate the aperture 184 to facilitate connection with the therapy device 124.

As described above, the porous conduit 120 may be coupled in fluid communication to the therapy device 124 utilizing, for example, the external end 180 of the porous conduit 120, or the conduit interface 495 and the multiple lumen conduit 497. The reduced-pressure source 188 may then be activated to deliver reduced pressure to the sealed space 140.

Upon application of the reduced pressure to the dressing 116 through the porous conduit 120, fluids from the tissue site 104 may be drawn into the manifold 128 and the porous conduit 120. In some embodiments, the system 100 may include a fluid canister (not shown) positioned in fluid communication between the central lumen 148 in the porous conduit 120 and the reduced-pressure source 188 in the therapy device 124 for capturing excess fluids. As fluids from the tissue site 104 enter the central lumen 148, the fluids may cause blockages by, for example, gelling or otherwise thickening within the central lumen 148. The interconnected pores 164 in the first porous wall 152 may provide a plurality of alternate fluid communication passageways that may be resistant to such blockages. Further, should a blockage occur in the first porous wall 152, the interconnected pores 164 and corresponding passageways may be sufficiently numerous to maintain fluid communication with the sealed space 140. In this manner, reduced pressure therapy may be reliably maintained with the tissue site 104. Further, instillation fluids from the instillation fluid source 190 that may be in fluid communication with the first porous wall 152 may travel reliability through the interconnected pores 164 to the tissue site 104. Similar to the interconnected pores 164 of the first porous wall 152, the interconnected pores 172 of the second porous wall 160 may provide a plurality of alternate fluid communication passageways that may be numerous and resistant to blockages. In this manner, the pressure sensor 192 that may be in fluid communication with the second porous wall 160 may provide an accurate pressure signal corresponding to the reduced pressure in the sealed space 140 of the dressing 116 for reliably controlling the reduced pressure. Further, the external surface area 142 of the insertion end 178 of the porous conduit 120 being disposed in the sealed space 140 and in fluid communication between the sealed space 140 and the pressure sensor 192 may enhance the reliability of the pressure signal generated by the pressure sensor 192.

Although this specification discloses advantages in the context of certain illustrative, non-limiting embodiments, various changes, substitutions, permutations, and alterations may be made without departing from the scope of the specification as defined by the appended claims. Further, any feature described in connection with any one embodiment may also be applicable to any other embodiment.

We claim:
1. A system for treating a tissue site, comprising:
a manifold adapted to be positioned proximate the tissue site;
a sealing drape adapted to cover the manifold and the tissue site to provide a sealed space between the sealing drape and the tissue site;
a porous conduit adapted to be in fluid communication with the manifold and the sealed space, comprising:
a central lumen,
a first porous wall substantially concentric about the central lumen, wherein the first porous wall has an open porous structure defining a plurality of interconnected pores in fluid communication with one another,
a barrier layer substantially concentric about the first porous wall, wherein the barrier layer is comprised of a non-porous material, and
a second porous wall substantially concentric about the barrier layer, wherein the second porous wall has an open porous structure defining a plurality of interconnected pores in fluid communication with one another, and wherein the barrier layer substantially precludes fluid communication laterally between the first porous wall and the second porous wall; and
a therapy device adapted to be in fluid communication with the porous conduit, wherein the porous conduit provides fluid communication between the manifold and the therapy device, fluid communication between the sealed space and the therapy device, or both.

2. The system of claim 1, wherein the manifold is adapted to distribute reduced pressure to the tissue site, and wherein the manifold is comprised of a porous, hydrophobic foam.

3. The system of claim 1, wherein the manifold is adapted to be positioned between the tissue site and the sealing drape.

4. The system of claim 1, wherein the sealing drape is comprised of a liquid impermeable material.

5. The system of claim 1, wherein the first porous wall and the second porous wall are each comprised of bonded particles that define the interconnected pores of the first porous wall and the interconnected pores of the second porous wall.

6. The system of claim 5, wherein the bonded particles are sintered polymer particles.

7. The system of claim 1, wherein the non-porous material comprising the barrier layer is liquid impermeable and hydrophobic.

8. The system of claim 1, wherein the porous conduit has a plurality of longitudinal depressions and a plurality of longitudinal protrusions disposed about an external circumference of the porous conduit and extending lengthwise along a length of the porous conduit.

9. The system of claim 1, wherein the porous conduit has an oval cross-sectional shape.

10. The system of claim 1, wherein the porous conduit has a length and an external circumference defining an external surface area that is disposed in the sealed space and in fluid communication with the manifold and the sealed space.

11. The system of claim 10, wherein the second porous wall defines the length and the external circumference of the porous conduit.

12. The system of claim 1, wherein the central lumen and the first porous wall are each in fluid communication with the manifold and the sealed space.

13. The system of claim 1, wherein the therapy device comprises a reduced-pressure source, a fluid source, and a pressure sensor, wherein the reduced-pressure source is in fluid communication with the central lumen, wherein the fluid instillation source is in fluid communication with the first porous wall, and wherein the pressure sensor is in fluid communication with the second porous wall.

14. The system of claim 1, wherein the porous conduit has an insertion end positioned within the sealed space and an external end positioned exterior to the sealed space, the external end further comprising an external barrier layer positioned substantially concentric about the second porous wall, wherein the external barrier layer is comprised of a non-porous, liquid impermeable material, and wherein the external end of the porous conduit is coupled in fluid communication to the therapy device.

15. The system of claim 14, wherein the external end of the porous conduit protrudes through an aperture in the sealing drape, and wherein the system further comprises a sealing collar sealingly engaged between the aperture in the sealing drape and the external end of the porous conduit.

16. The system of claim 1, further comprising a conduit interface adapted to be coupled in fluid communication between the porous conduit and the therapy device, Wherein the porous conduit is positioned in the sealed space proximate an aperture in the sealing drape, and wherein the conduit interface is adapted to be coupled to the porous conduit through the aperture, and wherein the conduit interface is adapted to sealingly engage the sealing drape about the aperture in the sealing drape.

17. The system of claim 16, further comprising a multiple lumen conduit coupled in fluid communication between the conduit interface and the therapy device, wherein the therapy device comprises a reduced-pressure source, a fluid instillation source, and a pressure sensor, and wherein the conduit interface and the multiple lumen conduit each provide a reduced-pressure lumen in fluid communication between the central lumen and the reduced-pressure source, a fluid instillation lumen in fluid communication between the first porous wall and the fluid instillation source, and a sensing lumen in fluid communication between the second porous wall and the pressure sensor.

18. The system of claim 1, wherein the porous conduit is disposed into the manifold.

19. The system of claim 1, wherein the porous conduit is disposed in the sealed space.

20. A system for treating a tissue site, comprising:
a manifold adapted to be positioned proximate the tissue site and to distribute reduced pressure to the tissue site;
a sealing drape adapted to cover the manifold and the tissue site to provide a sealed space between the sealing drape and the tissue site;
a porous conduit adapted to be disposed in the sealed space in fluid communication with the manifold and the sealed space, comprising:
a central lumen,
a first porous wall substantially concentric about the central lumen, wherein the first porous wall has an open porous structure defining a plurality of interconnected pores in fluid communication with one another, wherein the first porous wall is comprised of bonded particles defining the interconnected pores, and wherein the bonded particles are sintered polymer particles,
a barrier layer substantially concentric about the first porous wall, wherein the barrier layer is comprised of a non-porous, liquid impermeable material, and
a second porous wall substantially concentric about the barrier layer, wherein the second porous wall has an open porous structure defining a plurality of interconnected pores in fluid communication with one another, wherein the second porous wall is comprised of bonded particles defining the interconnected pores, wherein the bonded particles are sintered polymer particles, and wherein the barrier layer substantially precludes fluid communication laterally between the first porous wall and the second porous wall; and a therapy device adapted to be in fluid communication with the porous conduit, comprising:

a reduced-pressure source, a fluid instillation source, and a pressure sensor, wherein the reduced-pressure source is in fluid communication with the central lumen, the fluid instillation source is in fluid communication with the first porous wall, and wherein the pressure sensor is in fluid communication with the second porous wall.

\* \* \* \* \*